United States Patent [19]

Buck

[11] 4,307,078

[45] Dec. 22, 1981

[54] SULFONATED BIS(ALKYLPHENOXY)ALKANES AS DENTAL PLAQUE BARRIERS

[75] Inventor: Carl J. Buck, Berkeley Heights, N.J.

[73] Assignee: Johnson & Johnson Products Inc., New Brunswick, N.J.

[21] Appl. No.: 172,492

[22] Filed: Jul. 25, 1980

[51] Int. Cl.$^3$ .......................... A61K 7/16; C07F 3/06; C07C 143/42

[52] U.S. Cl. ................................. 424/56; 260/429.9; 260/512 R; 260/448 R

[58] Field of Search ...................... 424/56, 289, 315; 260/429.9, 512 R, 448 R

[56] References Cited

U.S. PATENT DOCUMENTS 3,812,178   5/1974   Weedon .............................. 260/512

*Primary Examiner*—Alan Siegel
*Attorney, Agent, or Firm*—Irving Newman

[57] ABSTRACT

Compounds useful in compositions and methods for preventing the attachment of dental plaque to the surfaces of the teeth of mammals comprise certain sulfonated bis(alkylphenoxy)alkanes and the pharmaceutically acceptable salts thereof. They are used in pharmaceutically acceptable vehicles that are periodically applied to teeth.

5 Claims, No Drawings

SULFONATED BIS(ALKYLPHENOXY)ALKANES AS DENTAL PLAQUE BARRIERS

TECHNICAL FIELD

This invention relates to certain sulfonated aromatic compounds, oral hygiene compositions comprising the compounds and to methods using such compositions to prevent attachment of bacteria to teeth. More particularly it relates to certain sulfonated bis(alkylphenoxy)alkanes that have been found useful in inhibiting the agglutination of oral microbes on teeth.

BACKGROUND ART

The prevention of the deposition of dental plaque on teeth is a highly desired result. Dental plaque results when cariogenic bacteria aggregate in colonies on the surface of teeth and form a tenacious deposit thereon. The presence of plaque on teeth is believed to be a precursor to development of gingivitis, dental caries and periodontal disease.

While many attempts have been made to control the effects of cariogenic bacteria and the dental plaque they produce, for example, by fluoride, flossing, brushing, etc., treatments, these are typically directed to either counteracting the secondary effects of plaque on the teeth and gums, or to the removal of plaque that is already formed on and adhering to the teeth and surrounding tissue. Such treatments are not, however, entirely successful, and must be supplemented with periodic treatment by dental professionals. To date, there is no commercially feasible home treatment method for preventing the formation of plaque or its adhesion to teeth.

THE INVENTION

Hydrophilic sulfonic acid salt derivatives of certain bis-(alkylphenoxy)alkanes have been synthesized and found to inhibit the deposition of dental plaque onto human teeth. The bis(alkylphenoxy)alkane sulfonates of this invention are substantially soluble in water or water/organic solvent vehicles and are applied to teeth from various dentifrice formulations, mouth rinses, or other oral hygiene procedures. While the mechanism of action of these sulfonated derivatives in retarding plaque deposition is not known with absolute certainty, it is presumed that films of the anionically charged compounds are deposited on teeth. A mutual repulsion effect is thought to arise between the negatively charged microorganisms responsible for plaque generation and the negatively charged films of bis(alkylphenoxy)alkane sulfonates. The bis(alkylphenoxy)alkane sulfonates of this invention are especially effective as components of dentifrices and other oral hygiene preparations in reducing dental plaque deposition on teeth.

A particular feature of the bis(alkylphenoxy)alkane sulfonates of this invention, which appears to govern their effectiveness as agents for the reduction of plaque deposition, is the balance between the hydrophobic and hydrophilic properties of these compounds. The hydrophobic groups in the bis(alkylphenoxy)alkane sulfonates are phenyl rings, substituent alkyl groups, and the alkylene linking group $[(CH_2)_n]$. The sulfonate group is the hydrophilic moiety. Accordingly, it has been found expedient to adjust the hydrophobic/hydrophilic balance in the bis(alkylphenoxy)-alkane sulfonates of this invention by independently varying both the size of the hydrophobic alkyl group and the chain length of the alkylene linking group, while maintaining the number of sulfonate groups at two per molecule.

The sulfonated derivatives which are useful for dental plaque control in accordance with the present invention are sulfonated alpha, omega-bis(alkylphenoxy)alkanes and salts thereof having structure (A),

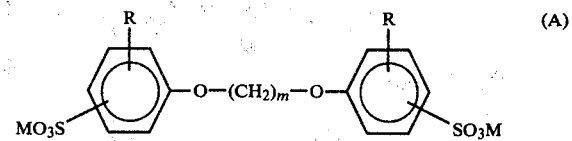

wherein R is a linear or branched alkyl having 2 to 20 carbon atoms, n is an integer from 2 to 12, and M is selected from the group consisting of hydrogen, lithium, sodium, potassium, calcium, magnesium, zinc, aluminum, ammonium and the substituted ammonium ions derived from pharmaceutically acceptable organic amines; provided that R and n are so selected that the weight percent of the sulfonate groups ($SO_3M$) in structure (A) is in the range of about 18% to 35%. Due to the relatively high acidity of the free acids (wherein M is hydrogen) it is preferred that they be converted to the less acidic salts for use in the oral hygiene compositions of this invention. Table 1 illustrates the relationship that must be maintained between the number of carbon atoms in substuent group R and the length (n) of the alkylene linking group in the bis(alkylphenoxy)alkane sulfonates of this invention [structure (A)] in order to achieve the requried 18–35% by weight sulfonate group concentration.

TABLE 1

| n | Number of Carbon Atoms in R |
|---|---|
| 2 | 7–20 |
| 4 | 5–20 |
| 6 | 5–20 |
| 8 | 4–20 |
| 10 | 2–20 |
| 12 | 2–20 |

The sulfonated alpha, omega-bis(alkylphenoxy)alkanes of this invention can be synthesized readily by a process consisting of (1) reaction of an alkali metal salt of an alkylphenol with an alpha, omega-dihaloalkane to afford the alpha, omega-bis(alkylphenoxy)alkane of structure (B), and (2) aromatic sulfonation of compounds of structure (B) to the disulfonic acid derivatives of structure (C). To obtain the salts of the disulfonic acids [compounds of structure (A) wherein M is other than hydrogen], the compounds of structure (C) are converted to the desired metal, ammonium, or substituted ammonium salts by neutralization and/or ion-exchange reactions known in the art. The general synthetic sequence for preparation of the disulfonic acid derivatives is shown schematically in equations (1) and (2):

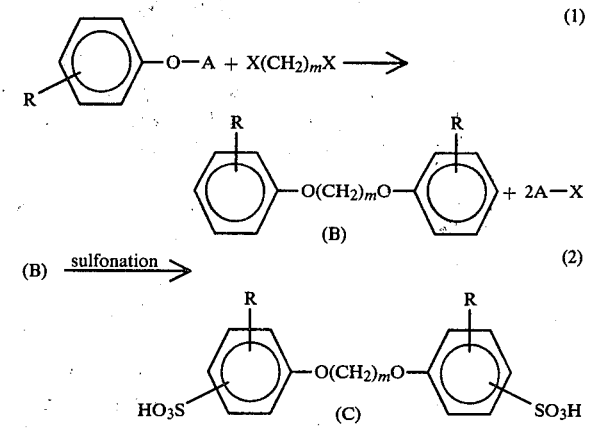

wherein
A = sodium or potassium
X = chlorine, bromine, or iodine

The synthetic scheme outlined above is essentially identical to that reported by M. J. Rosen, M. Baum, and F. Kasher [Journal of the American Oil Chemists' Society, Volume 53, pp. 742–745] for the synthesis of the corresponding symmetrical disodium sulfonates of structure (D), which contain no alkyl substituents on the phenyl rings.

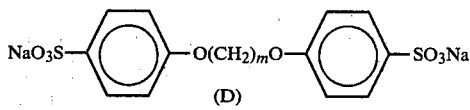

The alkylphenol precursors of the sodium or potassium alkyl phenoxide starting materials of equation (1) above are either readily available as items of commerce or synthesized by methods well known to those skilled in the art. The alkyl group may be either a linear or branched alkyl. Mixtures of compounds containing branched alkyl and linear alkyl groups are generally produced during synthesis, particularly among the longer-chain alkylphenols, such as the nonylphenol and dodecylphenol available from the General Aniline and Film Corp., and sold in such form. Such mixtures are suitable for use in the practice of this invention. In addition, the position of the alkyl group on the phenyl ring, relative to the phenolic hydroxyl group, can also be varied.

The dihaloalkanes used as co-reactants with the phenolic salts in the synthesis of the bis(alkylphenoxy)alkanes, according to equation (1), are often readily available items of commerce. If not, they can be synthesized easily by well-known organic reaction processes. Examples of useful dihaloalkanes are 1,2-dibromoethane; 1,4-dibromobutane; 1,5-dichloropentane; 1,6-diiodohexane; 1,8-dibromooctane; 1,10-dibromodecane; and 1,12-dibromododecane.

Sulfonation of the bis(alkylphenoxy)alkanes can be effected with such reagents as concentrated sulfuric acid, oleum, chlorosulfonic acid and liquid sulfur trioxide. The sulfonations are generally effected in inert solvents, such as methylene chloride, chloroform, and 1,2-dichloroethane; at temperatures of 40° C. or below; and using at least two moles of the sulfonation agent per mole of bis-(alkylphenoxy)alkane. The preferred sulfonation agents are chlorosulfonic acid and liquid sulfur trioxide.

The position of sulfonation on the phenyl rings of the bis(alkylphenoxy)alkane intermediates is generally not known with certainty and, in any event, is not considered important in the practice of this invention. The structures of the disulfonic acid and disulfonate salt compounds of this invention can be characterized by a number of known methods: (1) NMR and IR spectroscopic analysis, (2) acidimetric assays (on the sulfonic acid derivatives), (3) metal salt analysis via atomic absorption, and (4) elemental analysis.

The alkali metal salts of the sulfonated bis(alkylphenoxy)alkanes are conveniently prepared by neutralization of a water or alcohol solution of the sulfonic acid derivative with alkali metal hydroxide solutions to the potentiometric endpoint. The salts are recovered by filtration, solvent stripping, or freeze drying, depending on the type of solvent used and whether the salt precipitates directly from the solvent medium. Alternatively, sulfonate salts can be prepared by addition of at least stoichiometric quantities of an alkali metal oxide, carbonate, acetate, chloride, nitrate, or sulfate to the sulfonic acid derivative. The salts either precipitate directly, or are isolated by solvent stripping.

Multivalent metal salts, such as the calcium, magnesium, zinc, and aluminum salts, of the sulfonated products are prepared by methods similar to those described above. In an alternate procedure, multivalent metal salts can be prepared by an ion-exchange reaction between the multivalent ion and either the free sulfonic acid or an alkali metal sulfonate derivative. Ammonium salts of the sulfonic acid derivatives can be prepared by direct addition of ammonia or a primary, secondary, or tertiary organic amine.

The hydrophilic sulfonates of this invention are highly effective in reducing the deposition of plaque during in vitro testing when a suitable balance of hydrophobic and hydrophilic properties is provided in accordance with the foregoing definitions for structure (A).

Examples illustrating the effect of the hydrophobic/hydrophilic balance on the plaque barrier properties of the bis(alkylphenoxy)alkane sulfonates are found in Table 2, in which are summarized the results of tests carried out in accordance with the procedure described below.

The in vitro test procedure employed for obtaining the data in Table 2 begins with growth of plaque in small jars containing sterilized trypticase media that has been supplemented with sucrose. Typically, ten jars are individually inoculated with 0.5 ml of unpooled freshly collected human plaque from 10 subjects. In a control series, a presterilized glass slide or an extracted human tooth is inserted into each jar. In the test series, the tooth or glass slide is pretreated with a 1% solution of the test compound (dissolved in water or other vehicle), allowed to dry in order to deposit a thin flim of the compound on the surface, and the glass slide or tooth placed in the growth media. The jars are incubated under anaerobic conditions for two days at 37° C. The tooth or glass slide is removed, air dried, and stained with 0.15% FD&C #3 red dye solution to reveal the accumulated plaque deposits. The tooth or glass slide is scored for plaque density on a 0 to 5 scale. Plaque barrier activity is reported as the % of average plaque reduction, as compared to appropriate controls for ten subjects. Plaque reduction of about 40% or more is considered significant in this test.

TABLE 2

Plaque Barrier Properties of Bis(Alkylphenoxy)Alkane Disulfonates $$\text{NaO}_3\text{S}-\underset{R}{\text{C}_6\text{H}_3}-\text{O}(\text{CH}_2)_m\text{O}-\underset{R}{\text{C}_6\text{H}_3}-\text{SO}_3\text{Na}$$

| n | R | SO₃Na, % w/w | % Plaque Reduction |
|---|---|---|---|
| 4 | H | 46 | Inactive |
| 8 | H | 41 | Inactive |
| 12 | H | 37 | Inactive |
| 4 | Nonyl | 32 | 85 |
| 4 | Dodecyl | 28 | 83 |

As seen from Table 2 above, the first three listed products of structure (D) where n was 4, 8, and 12, were inactive in that they did not retard deposition of dental plaque. These compounds are outside the scope of the present invention both because they do not have an R group having 2 to 20 carbon atoms and because they do not contain the required 18–35 weight percent of sulfonate groups.

EXAMPLE 1

Synthesis of 1,4-Bis (Nonylphenxoy) butane

With stirring under nitrogen, 5.1 g (0.22 mole) sodium metal was added slowly to 100 ml. absolute ethanol. When all of the sodium had dissolved, a solution of 48.5 g (0.22 mole) nonylphenol (General Aniline and Film) in 50 ml. absolute ethanol was added all at once. The solution was heated to reflux and 21.6 g (0.100 mole) 1,4-dibromobutane added over about two hours. The reactor contents were transferred to a separatory funnel and the organic liquid phase which separated was extracted into 300 ml. hexane. The combined hexane extracts were washed by extraction with 5×100 ml. water, dried over magnesium sulfate, and solvent stripped to a viscous yellow liquid weighing 52.0 g. The latter was distilled in vacuo to remove recovered nonylphenol and other by-products (9.4 g total) boiling at 119° C. (0.2 mm) to 182° C. (0.1 mm). The yellow syrupy residue in the distillation pot was 41.3 g of the desired 1,4-bis (nonylphenoxy) butane.

EXAMPLE 2

Sulfonation of 1,4-Bis (nonylphenoxy) butane

A solution of 4.0 g (0.05 mole) liquid sulfur trioxide in 20 ml. methylene chloride was added over about 30 minutes at 21°–29° C. to a stirred solution of 9.9 g (0.02 mole) 1,4-bis (nonylphenoxy) butane (Example 1) in 100 ml. methylene chloride. After stirring within a temperature range of 24°–29° C. for another four hours, the reaction contents were stripped free of solvent to give 13.7 g of a red syrupy liquid. The latter was dissolved in 130 ml. methanol and neutralized with 110 ml. 0.520 N methanolic sodium hydroxide. After removal of the solvent, the residue was heated in 95% ethanol, the suspension cooled to room temperature, filtered to remove a small amount of solids (probably sodium sulfate), and the filtrate stripped free of solvent again. The residue was slurried in hot hexane and the yellow solids filtered, washed, and dried to give 9.9 g of the disodium sulfonate derivative of the bis (nonylphenoxy) butane.

EXAMPLE 3

Synthesis of 1,4-Bis (dodecylphenoxy) butane

In a manner analogous to the procedure described in Example 1, 46.6 g of 1,4-bis (dodecylphenoxy) butane were prepared from 5.1 g (0.22 mole) sodium metal, 57.7 g (0.22 mole) dodecylphenol (General Aniline and Film), and 21.6 g (0.100 mole) 1,4-dibromobutane. NMR analysis indicated that the dodecyl groups were branched alkyl groups and substituted largely in the position para to the phenoxy oxygen atom.

EXAMPLE 4

Sulfonation of 1,4-Bis (dodecylphenoxy) butane

In a manner analogous to the procedure described in Example 2, a solution of 11.6 g (0.02 mole) 1,4-bis (dodecylphenoxy) butane (Example 3) in 116 ml. methylene chloride was sulfonated with 4.0 g (0.05 mole) liquid sulfur trioxide. The crude disulfonic acid derivative was dissolved in methanol and neutralized with methanolic sodium hydroxide and 13.2 g disodium sulfonate derivative isolated. The D.S. was found to be 2.1 via NMR analysis.

EXAMPLE 5

Disodium Sulfonate of 1,2-Bis (eicosylphenoxy) ethane

Using procedures similar to those described in Examples 1 and 2, 1,2-bis (eicosylphenoxy) ethane is prepared from the sodium salt of eicosylphenol (2 molar equivalents) and 1,2-dibromoethane (1 molar equivalent) and then sulfonated and neutralized to afford the disodium sulfonate derivative.

EXAMPLE 6

Dipotassium Sulfonate of 1,8-Bis (butylphenoxy) octane

Two molar equivalents of the potassium salt of butylphenol and one molar equivalent of 1,8-dibromooctane are reacted in ethanol according to the procedure described in Example 1, to afford 1,8-bis (butylphenoxy) octane. Sulfonation with sulfur trioxide or chlorosulfonic acid, followed by neutralization of the disulfonic acid with methanolic potassium hydroxide, affords the potassium sulfonate.

EXAMPLE 7

Disodium Sulfonate of 1,12-Bis (4-ethylphenoxy) dodecane 1,12-bis (4-ethylphenoxy) dodecane is prepared from sodium 4-ethylphenoxide and 1,12-dichlorododecane, according to the method of Example 1, and sulfonated to the disulfonic acid derivative and neutralized with sodium hydroxide according to the method of Example 2, to afford the disodium sulfonate derivative.

The plaque barrier oral compositions of this invention may comprise any conventional pharmaceutically acceptable oral hygiene formulation that contains (and is compatible with) an effective amount of a plaque barrier agent as defined herein. Such formulations include, for example, mouthwashes, rinses, irrigating solutions, abrasive and nonabrasive gel dentifrices, denture cleansers, coated dental floss and interdental stimulator coatings, chewing gums, lozenges, breath fresheners, foams and sprays.

The plaque barrier agents may be present in these formulations in effective concentrations generally in the range of from about 0.05 weight percent to as much as 30 weight percent or the limit of compatibility with the vehicle. However, no advantage will be derived from concentrations in excess of about 20 weight percent. A preferred concentration range for the plaque barrier agents in the formulations of the invention is from about 0.5 to about 10 weight percent. A more preferred range is from about 2 to about 8 percent by weight, about 5% being the presently most preferred concentration in a nonabrasive gel vehicle.

The pH of these plaque barrier preparations should be between pH 5.0 and 10.0, preferably between pH 5.0 and 8.0, more preferably between about pH 6.0 and 7.5. Lower pH than 5.0 is undesirable because of the possible enhancement of enamel demineralization.

Suitable conventional pharmaceutically acceptable vehicles that can be employed with the plaque barrier agents to prepare the barrier compositions of this invention may comprise water, ethanol; such humectants as polypropylene glycol, glycerol and sorbitol; such gelling agents as cellulose derivatives, for example, Methocel, carboxymethylcellulose (CMC 7MF) and Klucel HF, polyoxypropylene/polyoxyethylene block copolymers, for example, Pluronic F-127, Pluronic F-108, Pluronic P-103, Pluronic P-104, Pluronic P-105, and Pluronic P-123, colloidial magnesium aluminosilicate complexes such as Veegum, and mucoprotein thickening agents such as Carbopol 934; gel stabilizers such as the silicon dioxides, for example, Cab-O-Sil M5, and polyvinylpyrrolidone; sweeteners such as sodium saccharin; preservatives such as citric acid, sodium benzoate, cetylpyridinium chloride, potassium sorbate, methyl and ethyl parabens; detergents such as sodium lauryl sulfate, sodium cocomonoglyceride sulfonate, sodium lauryl sarcosinate and polyoxyethylene isohexadecyl ether (Arlasolve 200) and approved colors and flavors.

The following specific examples will serve further to illustrate the plaque barrier compositions of this invention.

EXAMPLE A

Mouthwash Solution

| Barrier Agent | 0.5–2.0% w/w |
|---|---|
| Glycerol (humectant) | 6.0 |
| Pluronic F-108 | 1.0 |
| Sodium saccharin (sweetener) | 0.3 |
| Deionized Water | q.s. |
| Flavors | 1.0 |
| | 100.0 |

EXAMPLE B

Mouthwash Solution

| Plaque Barrier Agent | 0.5–3.0% w/w |
|---|---|
| Ethanol, USP | 15.0 |
| Pluronic F-108 (foaming agent) | 2.0 |
| Glycerol (humectant) | 10.0 |
| Sorbitol (humectant) | 10.0 |
| Sodium saccharin (sweetener) | 0.2 |
| Deionized Water | q.s. |
| Flavors | 0.2 |
| | 100.0 |

EXAMPLE C

Abrasive Dentrifice Gel

| Plaque Barrier Agent | 2.0–10.0% w/w |
|---|---|
| Fumed Silica (abrasive) | 55.0 |
| Sodium Lauryl Sulfate (detergent) | 1.5 |
| Glycerol (humectant) | 10.0 |
| Carboxymethylcellulose (gelling agent) | 2.0 |
| Sodium saccharin (sweetener) | 0.2 |
| Sorbitol (humectant) | 10.0 |
| Flavors | 1.0 |
| Deionized Water | q.s. |
| Preservative | 0.05 |
| | 100.0 |

EXAMPLE D

Chewing Gum

| Plaque Barrier Agent | 1.0–11.0% w/w |
|---|---|
| Gum Base | 21.3 |
| Sugar | 48.5–58.5 |
| Corn Syrup (Baume 45) | 18.2 |
| Flavors | 1.0 |
| | 100.0 |

EXAMPLE E

Nonabrasive Gel Dentifrice

| Plaque Barrier Agent | 0.05–30.0% w/w |
|---|---|
| Sorbistat (preservative) | 0.15 |
| Deionized Water | q.s. |
| Silicon Dioxide (gel stabilizer) | 1.0 |
| Pluronic F-127 (gelling agent) | 20.0 |
| Sodium Saccharin | 0.2 |
| Flavors | 1.5 |
| | 100.0 |

EXAMPLE F

The following formulation illustrates a presently preferred nonabrasive gel composition containing a barrier agent in accordance with the present invention.

| Ingredients | % w/w | |
|---|---|---|
| Distilled Water | q.s. | |
| Sodium Saccharin (sweetener) | 0.20 | |
| Sodium Benzoate (preservative) | 0.30 | |
| FD & C Blue #1 (0.1% aq. soln.) | 0.27 | |
| D & C Yellow #10 (0.5% aq. soln.) | 0.50 | |
| Gelling agent | 18.00 | |
| Glycerol (Humectant) | 20.00 | |
| Cab-O-Sil M5 (Silicon Dioxide) | 1.00 | |
| Plaque Barrier Agent | 5.00 | (dry basis) |
| Flavor | 0.80 | |
| | 100.0 | |

While the details of preparing all of the above formulations are well within the skill of the art, a suggested procedure for preparing the gel formulation of this example will be described for completeness.

In a first container the water, sodium saccharin, sodium benzoate and dyes are mixed. Then the container is put into an ice bath. When the temperature reaches 6° C., the gelling agent is added and the contents mixed slowly until the gelling agent is dissolved. Then the solution is heated to 70° C.

Into a second container is added the glycerin. Then the Cab-O-Sil M5 is sprinkled in with mixing. Then the plaque barrier agent is added and mixing continued to a smooth paste. The paste is then heated in a water bath with mixing to a temperature of 70° C.

The contents of the first container are added to the second container and blended together until the batch is homogenous while maintaining a 70° C. temperature. Then the flavoring is added, all mixing is stopped, and the formulation allowed to settle for approximately one hour. If necessary to remove air bubbles, overnight refrigeration may be employed.

These compositions are preferably employed from one to three times daily in a routine oral hygiene program to prevent the attachment of plaque to the teeth.

Variations can, of course, be made without departing from the spirit or scope of the invention.

I claim:

1. A sulfonated alpha, omega-bis(alkylphenoxy)alkane having structure (A),

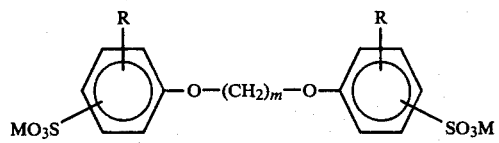

wherein R is a linear or branched alkyl having 2 to 20 carbon atoms, n is an integer from 2 to 12, and M is selected from the group consisting of hydrogen, lithium, sodium, potassium, calcium, magnesium, zinc, aluminum, ammonium and the substituted ammonium ions derived from pharmaceutically acceptable organic amines; provided that R and n are so selected that the weight percent of the (SO$_3$M) groups is between about 18% and about 35%.

2. An oral hygiene composition comprising an effective amount for preventing attachment of dental plaque to teeth of a sulfonated alpha,omega-bis(alkylphenoxy)alkane having structure (A),

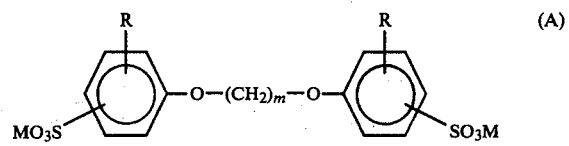

wherein R is a linear or branched alkyl having 2 to 20 carbon atoms, n is an integer from 2 to 12 and M is selected from the group consisting of lithium, sodium, potassium, calcium, magnesium, zinc, aluminum, hydrogen, ammonium, and substituted ammonium ions derived from pharmaceutically acceptable organic amines, provided further that R and n are so selected that the weight percent of the SO$_3$M groups is between about 18% and about 35% in a pharmaceutically acceptable oral hygiene vehicle compatible with said compound of structure (a).

3. The composition of claim 2 wherein M is a metal selected from the group consisting of potassium, lithium, sodium, calcium, magnesium, zinc and aluminum.

4. A method of preventing attachment of dental plaque to teeth comprising periodically applying to the teeth a composition of claim 2.

5. The method of claim 4 wherein said composition is applied from about 1 to about 3 times per day.

* * * * *